United States Patent [19]

Brethauer

[11] 4,187,719
[45] Feb. 12, 1980

[54] APPARATUS TO DETERMINE THE SEDIMENTATION RATE OF RED BLOOD CELLS

[75] Inventor: Ulrich Brethauer, Melsungen, Fed. Rep. of Germany

[73] Assignee: B. Braun Melsungen Aktiengesellschaft, Melsungen, Fed. Rep. of Germany

[21] Appl. No.: 929,287

[22] Filed: Jul. 31, 1978

[30] Foreign Application Priority Data

Aug. 11, 1977 [DE] Fed. Rep. of Germany ... 7724900[U]

[51] Int. Cl.² ...................... G01N 15/04; G01N 33/16
[52] U.S. Cl. ...................................... 73/61.4; 215/247
[58] Field of Search ......................... 73/61.4, 422 GC; 215/247; 233/26

[56] References Cited

U.S. PATENT DOCUMENTS

| 1,180,665 | 4/1916 | McElroy | 215/247 |
| 1,509,916 | 9/1924 | Waite | 215/247 X |
| 2,729,971 | 1/1956 | Stein | 73/61.4 |
| 3,233,727 | 2/1966 | Wilson | 215/247 |
| 3,823,840 | 7/1974 | Zackheim | 215/247 |
| 3,938,370 | 2/1976 | Kirsch et al. | 73/61.4 |

FOREIGN PATENT DOCUMENTS

| 916128 | 8/1954 | Fed. Rep. of Germany | 73/61.4 |
| 602763 | 6/1948 | United Kingdom | 215/247 |
| 1175428 | 12/1969 | United Kingdom | 215/247 |
| 1432833 | 4/1976 | United Kingdom | 73/422 GC |

*Primary Examiner*—Gerald Goldberg
*Assistant Examiner*—Joseph W. Roskos
*Attorney, Agent, or Firm*—Merriam, Marshall & Bicknell

[57] ABSTRACT

Apparatus for the determination of the sedimentation rate of red blood cells comprising a sedimentation tube adapted to hold a blood column, and a closure valve on one end of the sedimentation tube with said closure valve having a self-sealing valve means.

3 Claims, 2 Drawing Figures

APPARATUS TO DETERMINE THE SEDIMENTATION RATE OF RED BLOOD CELLS

This invention relates to apparatus for determining the sedimentation rate of red blood cells.

BACKGROUND OF THE INVENTION

According to the disclosure in Swiss Pat. No. 548,764, the sedimentation rate of red blood cells is determined according to the Westergren method by placing a 200 mm blood column in a transparent tube. Subsequently, the tube upper end is sealed with an inserted stopper which is used simultaneously for zero point adjustment and for suspension of the sedimentation tube in a holding apparatus. As such tubes are filled using syringes whose pistons slide unevenly or with a jerky movement, blood is unintentionally squirted or splashed out of the tube end. People, particularly those who carry out a multiplicity of blood examinations, are thereby exposed to the danger of infection by contaminated blood.

SUMMARY OF THE INVENTION

According to the subject invention there is provided novel apparatus for determining the sedimentation rate of red blood cells which has as one of its purposes the avoidance of the defects in the described prior art apparatus. The apparatus of the invention provides a closure valve at one end of the sedimentation tube, especially a Westergren tube, which makes it possible to readily inject blood into the tube and to fix the zero point automatically. The closure valve has a self-sealing valve means which, for example, can be a self-sealing perforation. The blood does not and/or cannot discharge from the tube upper end having the closure valve and the blood column is maintained automatically and safely at the original lever without later manually applying a separate closure or sealing apparatus on the tube upper end. Blood can be injected by a syringe into the tube end having the closure valve or into the other end. A means is provided on the tube end in which the blood is injected to tightly receive the conical end of a syringe to facilitate the injection.

The closure valve has one or more self-sealing perforations in the form of holes or slots which let air escape from the tube as blood, usually containing an added citrate salt, is injected into the tube. Use of a closure valve as described results in a back pressure build-up during filling of the blood sedimentation tube with a gradually decreasing air cushion so that during the injection of blood with syringes having pistons which operate in a jerky manner splashing is avoided and a smooth or uniform filling of the tube is achieved.

The closure valve is arranged so that when positioned on a tube a blood column therein will have a level which correlates with the zero mark of a scale on a blood sedimentation tube suspension apparatus.

The closure valve is desirably made of a transparent solid elastomeric material such as rubber or a similar material.

BRIEF DESCRIPTION OF THE DRAWINGS

The invention will be described further in conjunction with the attached drawings, in which.

DETAILED DESCRIPTION OF THE DRAWINGS

Figure 1:
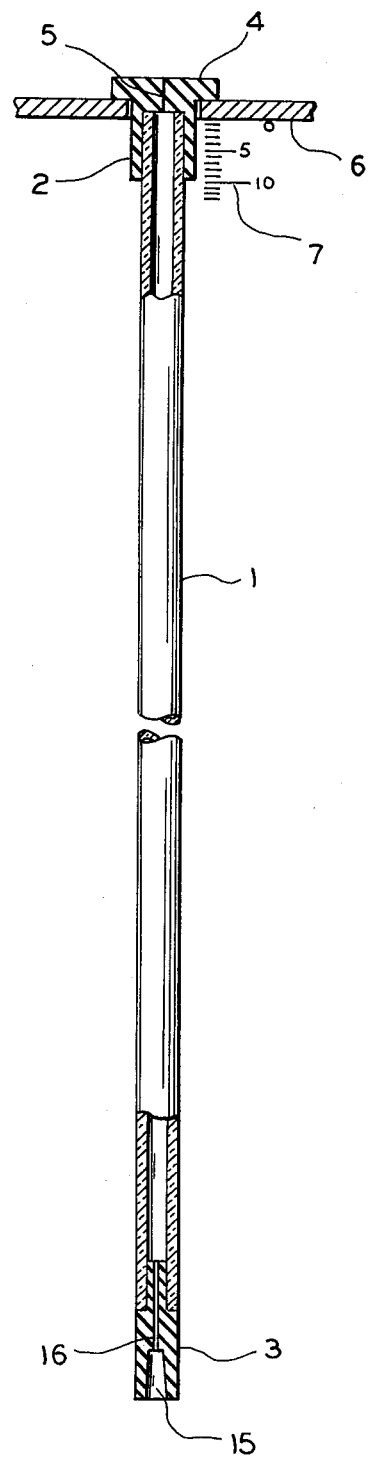
FIG. 1 is a longitudinal view of a Westergren blood sedimentation tube having one embodiment of a closure valve provided by the invention attached to the upper end of the tube with the tube to be filled through an extension plug on the other end.

With reference to FIG. 1, the Westergren blood sedimentation tube 1 has the closure valve 2 according to the invention pushed upon the upper end of the tube. An extension plug 3 is placed in the tube lower end. The extension plug desirably has an overall width no wider than that of the sedimentation tube. The extension plug 3 has a recess 15 with sloped or conical walls to accommodate a syringe conical end containing the blood to be examined. Orifice 16 extends from recess 15 into the tube interior space. The tube 1 is filled through the capillary orifice 16 in the extension plug 3. Closure valve 2 has a diaphragm-like portion 4 containing a self-sealing perforation 5 through which air located inside the tube 1 can escape during the filling. Perforation 5 recloses automatically when blood injection into the tube is terminated due to the elasticity of the material used for the membrane. The tubes filled in this manner with the blood to be examined are placed in a tube suspension holder with the 0-mark or zero point of the scale 7 and the blood level within the tube at the same level.

A blood column is injected into the apparatus of FIG. 1 up to the surface of closure valve 4 inside of the tube so that simultaneously the zero point on the measuring scale on the tube suspension holder 6 correlates with the blood level in tube 1. In the event the blood column reaches the closure valve and the user continues to exert pressure on the piston rod of the syringe, only very small quantities of blood can move toward the exterior through the perforation 5. After removing the syringe conical end from recess 15 in extension plug 3, the blood column in tube 1 is prevented by the closure valve 2 from oozing out with the tube suspended in the tube suspension apparatus 6 with the closure valve upward.

Figure 2:
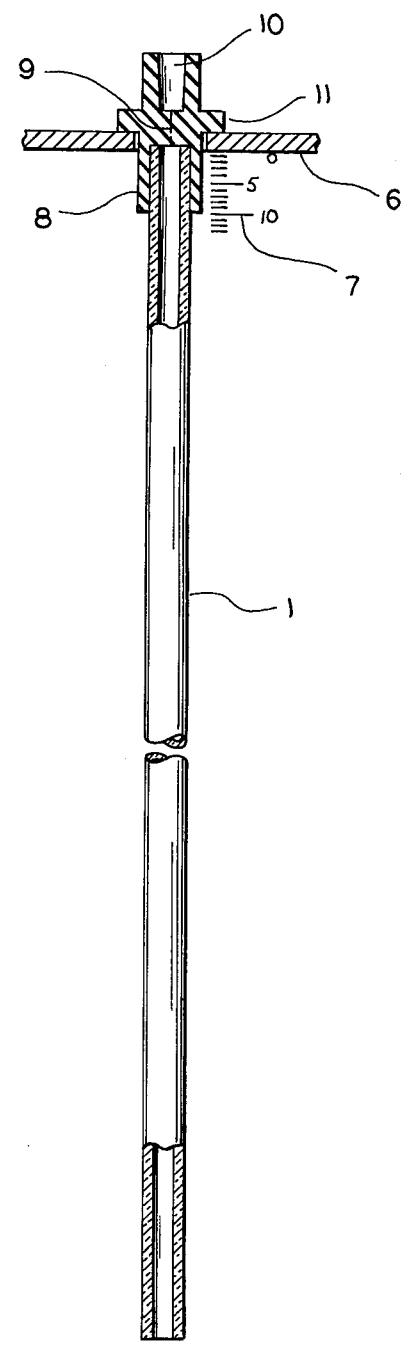
FIG. 2 is a longitudinal view of a Westergren blood sedimentation tube illustrating an embodiment of the apparatus of the invention in which the tube is filled through the closure valve.

FIG. 2 shows a second embodiment wherein the blood sediment tube 1 is not filled from the end opposite the tube end having the closure valve as in FIG. 1, but is filled through the same end having the closure valve itself. The closure valve 8 of elastomeric material, such as rubber, is provided with a recess 10 having sloped or conical walls into which the conical end of an injection syringe, customarily used in medicine, fits tightly. As blood in the syringe is ejected against the self-sealing perforation 9, the latter opens and the tube is filled with the required amount of blood. According to FIG. 2, when the tube 1 having the closure valve 8 is placed in the tube suspension holder 6 the level of the blood column in the tube is at the inner surface of the closure valve 8 in the tube and that surface is automatically positioned to be adjacent the zero mark of scale 7.

Both of the described apparatus eliminate the need to insert a stopper after blood is injected into the tube, so that the user avoids one additional operation previously required.

The closure valve desirably is manufactured from transparent elastomeric material so that identification of the zero point and reading of the first few millimeters of the scale can be readily achieved. A clear rubber is suitably used, such as a silicone rubber.

Although the apparatus has been described with specific reference to its use in blood testing, it should be recognized that the apparatus can have value for testing other liquids or dispersions.

What is claimed is:

1. Apparatus for the determination of the sedimentation rate of red blood cells, comprising:

a sedimentation tube adapted to hold a blood column, a closure valve of elastomeric material on one end of the sedimentation tube with said closure valve having a self-sealing perforation providing communication between the outside of the tube and the tube interior, said closure valve having a hollow recess surrounded by a wall into which recess the tube end tightly fits, and an extension plug, located in the other end of the tube, having a recess to receive the end of a syringe to inject liquid into the tube, and an orifice extending from the recess into the tube interior space.

2. Apparatus according to claim 1 in which the extension plug has an overall width no wider than that of the sedimentation tube.

3. Apparatus for the determination of the sedimentation rate of red blood cells, comprising:

a sedimentation tube adapted to hold a blood column, a closure valve of elastomeric material on one end of the sedimentation tube with said closure valve having a self-sealing perforation providing communication between the outside of the tube and the tube interior, said closure valve having a first hollow recess surrounded by a wall into which recess the tube end tightly fits, and said closure valve having a second recess to receive the end of a syringe, and the second recess communicates with the self-sealing perforation so that liquid can be injected from a syringe into the tube.

* * * * *